United States Patent [19]

Dell'Aquila

[11] Patent Number: 5,045,309

[45] Date of Patent: Sep. 3, 1991

[54] QUICK DRYING NAIL POLISH

[76] Inventor: Louis Dell'Aquila, 54 Sherwood Ave., Englewood Cliffs, N.J. 07632

[21] Appl. No.: 457,420

[22] Filed: Dec. 27, 1989

[51] Int. Cl.5 .............................................. A61K 7/043
[52] U.S. Cl. ...................................... 424/61; 514/772; 514/789
[58] Field of Search ................... 424/61; 514/772, 789

[56] References Cited

U.S. PATENT DOCUMENTS

| 3,483,289 | 12/1969 | Michaelson et al. | 424/61 |
| 3,907,580 | 9/1975 | van Ham | 106/158 |
| 4,179,304 | 12/1979 | Rossomando | 106/177 |
| 4,301,046 | 11/1981 | Schlossman | 260/16 |
| 4,302,442 | 11/1981 | Socci et al. | 424/61 |
| 4,421,881 | 12/1983 | Benkendorf et al. | 524/24 |
| 4,601,901 | 7/1986 | Guillon et al. | 424/61 |
| 4,646,765 | 3/1987 | Cooper et al. | 424/61 X |

Primary Examiner—Thurman Page
Assistant Examiner—Susan S. Rucker
Attorney, Agent, or Firm—Kenyon & Kenyon

[57] ABSTRACT

A quick drying nail coating composition which contains conventional nail coating ingredients, for example, a film former, a resin, a plasticizer and a solvent and a compound which accelerates the drying time of the composition. The accelerator compound is a hydrocarbon which is chlorinated, fluorinated, fluorinated and chlorinated or mixtures thereof. The composition exhibits accelerated drying times when compared to nail coatings not containing the accelerator compound.

18 Claims, 1 Drawing Sheet

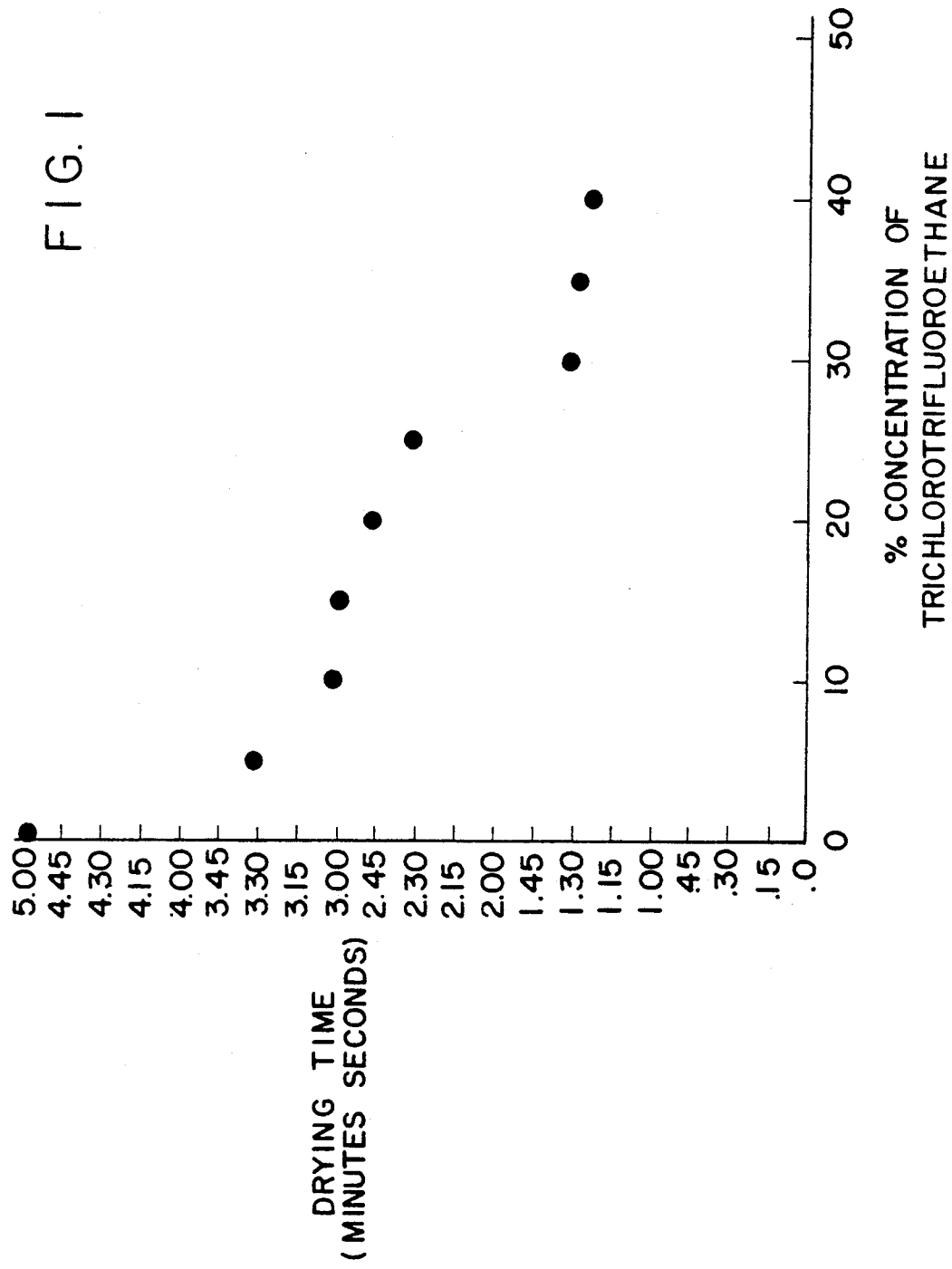

QUICK DRYING NAIL POLISH

FIELD OF THE INVENTION

The present invention relates to nail polish compositions which, when applied to human nails as a coating, provide a desirable improvement in the drying time of the nail coating. The present invention also relates to a method for preparing quick drying nail polish compositions.

BACKGROUND OF THE INVENTION

Numerous types of nail polishes are sold commercially. Liquid nail polish formulations typically contain a film former, usually nitrocellulose, a modifying resin such as toluene-sulfonamide-formaldehyde resin, a plasticizer, such as camphor, dibutylphthalate, etc. and one or more solvents such as toluol, lower aliphatic alcohols or acetates, etc. In addition, these formulations usually contain coloring agents and fragrances.

There are a number of desirable properties in nail polish compositions. In particular, a nail polish should dry and harden quickly, apply easily, be well adherent, glossy, waterproof and suitably colored, wear well, be elastic, resist chipping, peeling and abrasion for a reasonable period of time, and be dermatologically innocuous.

One important property of a nail polish, which is addressed by the present invention, is the ability for a coating to dry rapidly once applied to a human nail since in applying nail polish to nails, multiple coatings are typically applied to improve coloring, gloss, wear resistance, etc. This coating process is time consuming since the first coating of nail polish must be dry before a subsequent coating can be applied to avoid smudging and damage to the first coating, and the average drying time for a coating of conventional nail polish is about five minutes. That is, five minutes must elapse between coating applications to prevent damage to a previous coating. Thus, the total time for completing the nail polishing process using conventional compositions can be in the order of 15 minutes or more.

OBJECTS AND SUMMARY OF THE INVENTION

It is therefore an object of the present invention to provide nail polish compositions which, when applied to human nails as a coating, provide a desirable improvement in the drying time of the coating.

It is another object of the present invention to provide nail polish compositions having improved drying times comprising a film former, a modifying resin, a plasticizer and an effective amount of a fluorinated and/or chlorinated hydrocarbon.

It is a further object of the invention to provide a method for substantially improving the drying time of conventional nail polish compositions.

In accordance with the present invention, it has been discovered that the addition of from about 25% to about 50% by volume of a fluorinated and/or chlorinated hydrocarbon, such as, for example, trichlorotrifluoroethane, in nail polish compositions will reduce the drying time of a nail coating by about 50% or more without adversely affecting other desirable properties of the composition, e.g., glossiness, color, durability, etc.

According to a preferred embodiment of the invention, the nail polish composition will comprise a film former, a modifying resin, a plasticizer, one or more solvents, and trichlorotrifluoroethane in an amount ranging from about 30 to 40% by volume based on the total volume of the nail polish composition.

The nail polish compositions of the present invention provide reduced drying times of from about 50% up to about 70% over conventional nail polish compositions without adversely affecting the other desirable properties of the nail polish coating.

BRIEF DESCRIPTION OF THE DRAWING

FIG. 1 is a graph demonstrating the improved drying time for nail polish compositions containing various concentrations of trichlorotrifluoroethane according to the present invention.

DETAILED DESCRIPTION OF THE INVENTION

The present invention provides nail polish compositions having reduced drying times suitable for application as coatings for human nails.

In accordance with the present invention, an effective amount of fluorinated and/or chlorinated hydrocarbon is added to a conventional nail polish formulation to provide the improved drying times.

In general, conventional nail polish compositions are comprised of a film former, one or more modifying resins, a plasticizer, colorants and the balance liquid carriers such as solvents, couplers and diluents.

Film formers are the base material for modern nail polish. Film forming substances are selected for their hardness, toughness, resistance to abrasion and ability to release solvent. Nitrocellulose is a commonly used film former.

Resins cooperate with nitrocellulose-based polishes to improve the degree of film build and enhance depth, gloss and adhesion. Suitable resin materials include shellac and pontianak, as well as synthetics such as acrylic copolymers polyvinyl acetate, butyrates, and arylsulfonamide-formaldehyde.

Plasticizers commonly used in nail polish compositions include tricresyl phosphate, dibutyl phthalate, butyl phthalyl, butyl glycolate, dioctyl phthalate, triphenyl phosphate, dibutoxy ethyl phthalate, camphor, castor oil, benzyl benzoate, tributyl phosphate, butyl acetyl ricenoleate, butyl stearate, triethyl citrate, dibutyl tartrate and diamyl phthalate.

Solvents used in nail polish compositions containing nitrocellulose include ketones, esters, amides, glycolethers and nitroparaffins.

Couplers are typically alcohols which increase the strength of the active solvents. These include ethanol, propanol, isopropanol, n-botylalcohol and mixtures thereof.

Commonly used diluents include aromatic or aliphatic hydrocarbons, such as toluene and xylene.

Inorganic pigments such as titanium dioxide, aluminum silicate, colored polymeric material and dyes may be used as colorants.

In conventional nail polish compositions, the nitrocellulose film former typically comprises up to about 15% to 20% by weight of the composition. When used, resins are added at a ratio of about two parts nitrocellulose to one part resin by weight.

Conventional nail polish compositions also contain plasticizers in amounts ranging from 20% to 50% by weight of the nitrocellulose present to achieve the requisite degree of flexibility. Pigments can account for 1% to 5% of the total solution. Up to 50% of the solvent used in conventional nail polish compositions may be a diluent.

According to the present invention, it has been discovered that the addition of an effective amount of a chlorinated and/or fluorinated hydrocarbon to a conventional nail polish composition significantly reduces nail polish drying time. Surprisingly, the drying time is dramatically reduced when a chlorinated and/or fluorinated hydrocarbon is added to a conventional nail polish composition at about 30% concentration by volume.

The present invention can be used in conjunction with conventional nail polish compositions or with one or more known film formers, resins, plasticizers, solvents and/or colorants within the following ranges by weight:
Film former: 10 to 20%
Resin: 0 to 10%
Plasticizer: 2 to 10%
Solvent: 38 to 50%
Colorant: 0 to 5%

EXAMPLE

In order to evaluate the quick drying nail polish compositions prepared according to the present invention, a series of nail polish samples containing various concentrations of the preferred hydrocarbon, trichlorotrifluoroethane were prepared and tested for drying times.

The nail polish composition used in this example is manufactured by L'Oreal and its ingredients are listed in Table 1 below. The entry called "other" refers to those compounds that appeared in trace amounts and could not be detected. The list of ingredients on the L'Oreal product container states that these other components may be one or more of the following: toluene-sulfonamide-formaldehyde resin, camphor, stearalkoniumhecktorite, citrate acid benzophenone, titanium dioxide, guanine, iron oxides, D & C red #6 barium lake, D & C red #34 calcium lake, D & C red #7 calcium lake, D & C yellow #5 aluminum lake, ferric ammonium ferrocyanide, tin oxide, bismuth oxychloride, [814].

TABLE 1

| Ingredient | Concentration (Weight %) |
| --- | --- |
| Toluene | 33.0% |
| Butyl Acetate | 30.0% |
| Ethyl Acetate | 16.0% |
| Isopropyl Alcohol | 0.5% |
| Nitrocellulose | 18.0% |
| Dibutyl Phthalate | 0.5% |
| Aluminum Silicate "Mica" | 1.7% |
| Other | 0.3% |
| Total | 100.0% |

The nail polish composition was divided into eight samples to which was added varying amounts of trichlorotrifluoroethane. The amount of trichlorotrifluoroethane added to each nail polish sample ranged from 5% to 40% by volume in 5% increments. The drying time for each sample was determined as follows:

Nail polish samples containing varying amounts of trichlorotrifluoroethane were applied to human finger nails as a thin coating using the applicator provided by the manufacturer at a temperature of 68° F. to 70° F. and at a moderate relative humidity. The nail polish samples were determined to be dry when they no longer smudged upon touching. The amount of time required for each nail polish sample to dry completely was recorded with a stop watch. The concentration of trichlorotrifluoroethane in each sample is reported as the volumetric ratio of trichlorotrifluoroethane in each sample to the total volume of the sample. The measured drying time was plotted against the trichlorotrifluoroethane volumetric concentration as shown in FIG. 1.

The test data illustrated in FIG. 1 demonstrates that the addition of trichlorotrifluoroethane to a conventional nail polish composition reduces the amount of time required for a nail coating to dry and harden.

Referring to FIG. 1, when no trichlorotrifluoroethane is added to the conventional nail polish, about 5 minutes is required for the nail coating to dry. When 25% by volume of the nail polish sample is made up of trichlorotrifluoroethane, about 2.5 minutes are needed for the coating to dry. At a concentration of 30% trichlorotrifluoroethane, drying time is unexpectedly and dramatically reduced to about 1.5 minutes. This represents a reduction in drying time of about 70% over conventional nail polish compositions. Furthermore, the nail polish samples containing up to 50% by volume of trichlorotrifluoroethane continue to provide the other desirable properties in a coating, e.g., hardness, durability, appearance, etc.

At trifluorotrichloroethane concentrations over 50% of the total volume, gelation or precipitation of the nitrocellulose film former occurs. Therefore, compositions containing about 25% to 50% of trichlorotrifluoroethane are preferred in accordance with the present invention to reduce nail polish drying time. Nail polish compositions containing about 30% to 40% of trichlorotrifluoroethane are most preferred.

As will be apparent to those skilled in the art, the present invention may be embodied in other specific forms without departing from the spirit or essential characteristics of the invention.

What is claimed is:

1. A quick drying nail polish composition comprising a film former, a resin, a plasticizer, a solvent, and a hydrocarbon which is effective to increase the rate at which said nail polish dries selected from the group consisting of fluorinated hydrocarbons, chlorinated hydrocarbons, and fluorinated and chlorinated hydrocarbons and mixtures thereof, wherein about 25 to 50% by volume of the total nail polish composition is the hydrocarbon.

2. The nail polish of claim 1 wherein the hydrocarbon is trichlorotrifluoroethane.

3. The nail polish composition according to claim 1 wherein about 30 to 40 percent by volume of the total nail polish volume is hydrocarbon.

4. The nail polish of claim 3 wherein the hydrocarbon is trichlorotrifluoroethane.

5. In a method for substantially improving the drying time of nail polish compositions, the improvement comprising the addition of from about 25 to 50% by volume of a hydrocarbon which is effective to increase the rate at which said nail polish dries selected from the group consisting of fluorinated hydrocarbons, chlorinated hydrocarbons, and fluorinated and chlorinated hydrocarbons and mixtures thereof, based on the total volume of the nail polish composition.

6. The method of claim 5 wherein the hydrocarbon is trichlorotrifluoroethane.

7. The method of claim 5 wherein the nail polish composition comprises a film former, a resin, a plasticizer, a solvent, and a colorant.

8. The method of claim 5 wherein about 30 to 40% by volume of the nail polish composition is trichlorotrifluoroethane.

9. A quick drying nail polish composition comprising from about 10 to 20% by weight film former, from about 0 to 10% by weight resin, from about 2 to 10% by weight plasticizer, from about 38 to 50% by weight solvent, from about 0 to 5% by weight colorant and from about 25 to 50% by volume of a hydrocarbon which is effective to increase the rate at which said nail polish dries selected from the group consisting of fluorinated hydrocarbons, chlorinated hydrocarbons, and fluorinated and chlorinated hydrocarbons and mixture thereof.

10. The nail polish of claim 9 wherein the hydrocarbon is trichlorotrifluoroethane.

11. A quick drying nail polish composition comprising a film former, a resin, a plasticizer, a solvent, and a hydrocarbon selected from the group consisting of fluorinated hydrocarbons, chlorinated hydrocarbons, and fluorinated and chlorinated hydrocarbons and mixtures thereof, said hydrocarbon being effective to increase the rate at which said nail polish dries.

12. The nail polish composition according to claim 11 wherein the hydrocarbon is present in an amount which is about 5% to 50% by volume of the nail polish composition.

13. The nail polish composition according to claim 11 wherein the hydrocarbon is trichlorotrifluoroethane.

14. The nail polish composition according to claim 11 wherein the nail polish composition comprises from about 10 to 20% by weight film former, from 0 to about 10% by weight resin, from about 2 to 10% by weight plasticizer, from about 38 to 50% by weight solvent and from 0 to about 5% by weight colorant.

15. The nail polish composition according to claim 12 wherein the nail polish composition comprises from about 10 to 20% by weight film former, from 0 to about 10% by weight resin, from about 2 to 10% by weight plasticizer, from about 38 to 50% by weight solvent and from 0 to about 5% by weight colorant.

16. The nail polish composition according to claim 13 wherein the nail polish composition comprises from about 10 to 20% by weight film former, from 0 to about 10% by weight resin, from about 2 to 10% by weight plasticizer, from about 38 to 50% by weight solvent and from 0 to about 5% by weight colorant.

17. The nail polish composition according to claim 12 wherein the hydrocarbon is trichlorotrifluoroethane.

18. The nail polish composition according to claim 3 wherein the hydrocarbon is a chlorinated and fluorinated hydrocarbon.

* * * * *